(12) United States Patent
Yuan et al.

(10) Patent No.: US 11,992,049 B2
(45) Date of Patent: May 28, 2024

(54) ELECTRONIC CIGARETTE

(71) Applicant: SHENZHEN FIRST UNION TECHNOLOGY CO., LTD., Shenzhen (CN)

(72) Inventors: Zhi Yuan, Shenzhen (CN); Zhongli Xu, Shenzhen (CN); Yonghai Li, Shenzhen (CN)

(73) Assignee: SHENZHEN FIRST UNION TECHNOLOGY CO., LTD., Shenzhen (CN)

( * ) Notice: Subject to any disclaimer, the term of this patent is extended or adjusted under 35 U.S.C. 154(b) by 542 days.

(21) Appl. No.: 17/298,667

(22) PCT Filed: Nov. 5, 2019

(86) PCT No.: PCT/CN2019/115747
§ 371 (c)(1),
(2) Date: May 31, 2021

(87) PCT Pub. No.: WO2020/108246
PCT Pub. Date: Jun. 4, 2020

(65) Prior Publication Data
US 2022/0015423 A1 Jan. 20, 2022

(30) Foreign Application Priority Data
Nov. 30, 2018 (CN) .......................... 201822001919.9

(51) Int. Cl.
A24F 40/10 (2020.01)
A24F 40/42 (2020.01)

(52) U.S. Cl.
CPC .............. *A24F 40/42* (2020.01); *A24F 40/10* (2020.01)

(58) Field of Classification Search
CPC ........... A24F 40/40; A24F 40/42; A24F 40/10
(Continued)

(56) References Cited

U.S. PATENT DOCUMENTS 9,302,825 B2 * 4/2016 Liu ...................... B65D 43/163
10,004,267 B2 * 6/2018 Liu .......................... H05B 3/16
(Continued)

FOREIGN PATENT DOCUMENTS

| CN | 104983076 A | 10/2015 |
|---|---|---|
| CN | 107951079 A | 4/2018 |

(Continued)

*Primary Examiner* — Harshad C Patel
(74) *Attorney, Agent, or Firm* — Cheng-Ju Chiang

(57) ABSTRACT

An electronic cigarette includes an outer housing. An atomizing sheath is received in the outer housing. An aerosol output passageway is defined between the outer housing and the atomizing sheath. An extending portion extends inwards from an inner wall of the atomizing sheath to divide the atomizing sheath into a first sleeve body and a second sleeve body for respectively storing atomizing liquid therein. The extending portion blocks incompletely the first sleeve body from the second sleeve body so that the first sleeve body and the second sleeve body are spatially communicated with each other. An atomizing core is disposed in the second sleeve body. An atomizing passageway is formed in the atomizing core. The extending portion forms therein an airflow path penetrating a wall of the atomizing sheath. The airflow path is used to spatially communicate the atomizing passageway with the aerosol output passageway.

10 Claims, 6 Drawing Sheets

Figure 1:
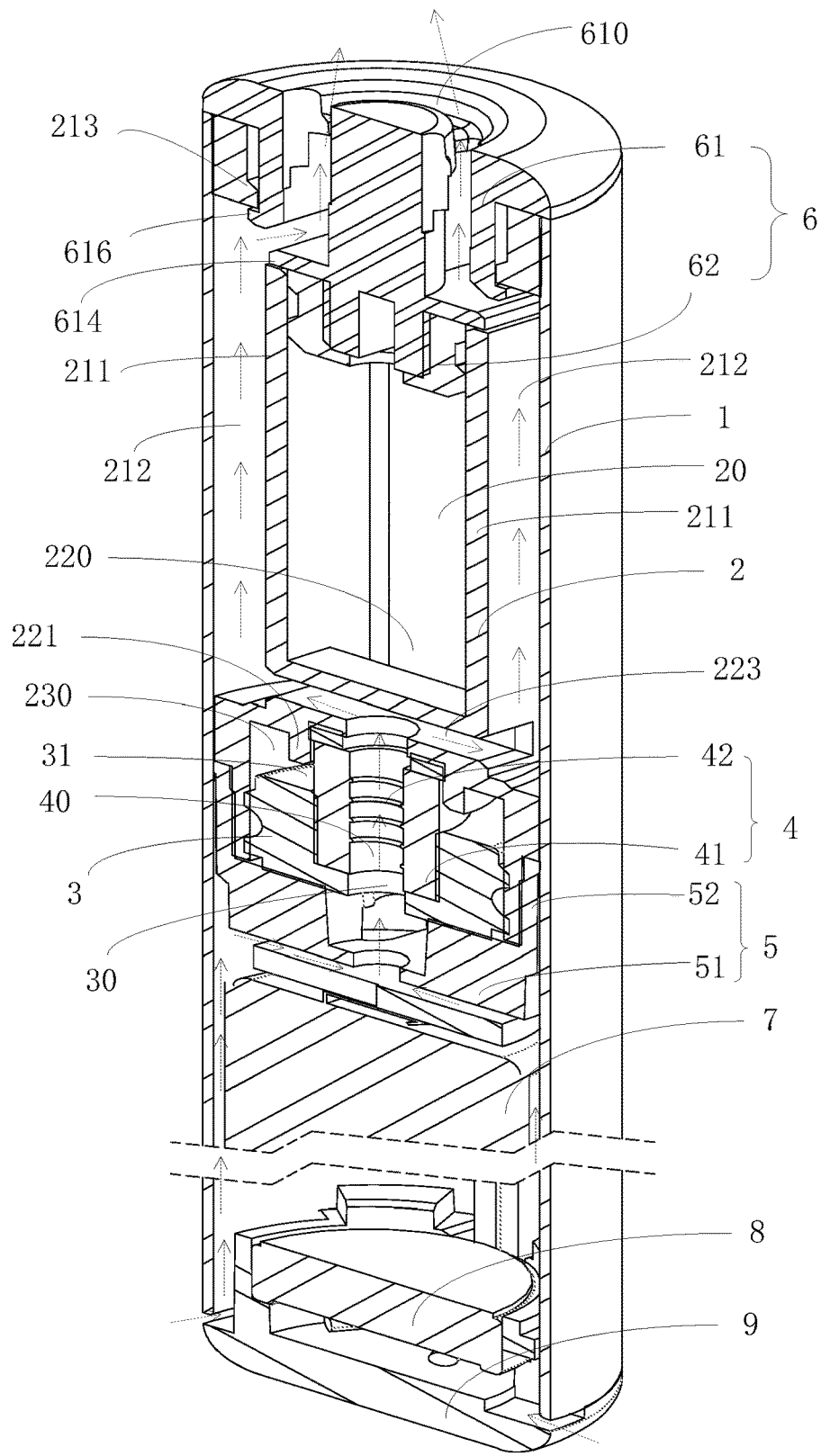

(58) Field of Classification Search
USPC .......................................................... 131/329
See application file for complete search history.

(56) References Cited

U.S. PATENT DOCUMENTS

| | | | |
|---|---|---|---|
| 10,015,986 B2* | 7/2018 | Cadieux | A24F 42/10 |
| 10,045,562 B2* | 8/2018 | Buchberger | A61M 11/042 |
| 10,314,340 B2* | 6/2019 | Davis | A24F 40/48 |
| 2014/0020697 A1* | 1/2014 | Liu | H02J 50/005 |
| | | | 320/108 |
| 2016/0374392 A1* | 12/2016 | Liu | A24F 40/51 |
| | | | 392/404 |
| 2018/0146707 A1* | 5/2018 | Chen | A24F 40/42 |
| 2020/0305506 A1* | 10/2020 | Borkovec | A24F 40/65 |

FOREIGN PATENT DOCUMENTS

| | | |
|---|---|---|
| CN | 207707306 U | 8/2018 |
| CN | 207767547 U | 8/2018 |
| CN | 207784278 U | 8/2018 |
| CN | 209234999 U | 8/2019 |
| CN | 209376699 U | 9/2019 |
| WO | 2018/170848 A1 | 9/2018 |

* cited by examiner

ELECTRONIC CIGARETTE

CROSS REFERENCE TO RELATED APPLICATIONS

The present application is a 35 U.S.C. § 371 National Phase conversion of International (PCT) Patent Application No. PCT/CN2019/115747, filed on Nov. 5, 2019, which claims priority of Chinese Patent Application No. 201822001919.9, filed on Nov. 30, 2018, the disclosure of which is incorporated by reference herein. The PCT International Patent Application was filed and published in Chinese.

BACKGROUND OF THE INVENTION

1. Field of the Invention

The present invention relates to a technical field of cigarette equipment, particularly relates to an electronic cigarette.

2. The Related Arts

Electronic cigarettes are electronic products that imitate cigarettes and have the same appearance, smoke, taste and feel as cigarettes. It is a product that allows users to inhale after atomization liquid containing nicotine is turned into aerosol via atomization, etc. Due to advantages of electronic cigarettes including convenient portability, lacking generation of open flames and environmental protection, electronic cigarettes are favored by many smokers.

An existing electronic cigarette generally includes an atomizing sleeve, a base, an atomizing core, and an air conductive tube. The base, the atomizing core, and the air conductive tube are all received in the atomizing sleeve. The base is located at a lower end of the atomizing sleeve. A lower end of the atomizing core is fixed on the base, and an upper end of the atomization core is connected with the air conductive tube. An upper end of the air conductive tube is connected with an air outlet of the atomization sleeve. A liquid storage cavity for storing atomization liquid is defined and formed between an inner wall of the atomization sleeve, an outer wall of the air tube and an outer wall of the atomization core. Aerosol produced in an atomization channel in the atomization core is discharged out of the electronic cigarette through the air conductive tube and the air outlet.

Since the atomization liquid of the above electronic cigarette is stored in the annular liquid storage cavity between the atomization sleeve and the air conductive tube, in the condition of an outline dimensions of the atomization sleeve being constant, a volume of the liquid storage cavity in the atomization sleeve is reduced by the air conductive tube received in the atomization sleeve. As a result, in order to increase the volume of the liquid storage cavity in the atomization sleeve, a structure design of the electronic cigarette to place an air outlet channel, which connects the atomization channel with the air outlet, outside the atomization sleeve is often adopted. However, how to discharge aerosol produced in the atomization channel in the atomization core received in the atomization sleeve into the air outlet channel outside the atomization sleeve becomes a problem to be solved urgently.

SUMMARY OF THE INVENTION

In order to solve the aforementioned technical problem of existing technology to discharge aerosol produced in the atomization channel in the atomization core received in the atomization sleeve out of the atomization sleeve, an electronic cigarette is provided in accordance with a preferred embodiment of the present invention to include the following.

The electronic cigarette includes an outer housing.

The electronic cigarette includes an atomizing sheath. The atomizing sheath is received in the outer housing. At least one aerosol output passageway is defined between the outer housing and the atomizing sheath.

The electronic cigarette includes an extending portion. The extending portion extends inwards from an inner wall of the atomizing sheath to divide the atomizing sheath into a first sleeve body and a second sleeve body for respectively storing atomizing liquid therein. The extending portion blocks incompletely the first sleeve body from the second sleeve body so that the first sleeve body and the second sleeve body are spatially communicated with each other.

The electronic cigarette further includes an atomizing core. The atomizing core is disposed in the second sleeve body. An atomizing passageway is formed in the atomizing core. The atomizing core is used to atomize the atomizing liquid for generating aerosol and releasing the generated aerosol into the atomizing passageway.

The extending portion is a hollow structure to form an airflow path penetrating a wall of the atomizing sheath. The airflow path is used to spatially communicate the atomizing passageway with the at least one aerosol output passageway.

Alternatively, the extending portion extends perpendicularly to a lengthwise direction of the atomizing sheath. A liquid storage cavity is formed in the first sleeve body. A transitional storage cavity is formed in the second sleeve body. A communicating through hole is disposed on the extending portion to spatially communicate the liquid storage cavity with the transitional storage cavity.

Alternatively, the first sleeve body includes two separating walls. The at least one aerosol output passageway is separated to become two aerosol output passageways respectively formed between the two separating walls and the outer housing. The two aerosol output passageways are respectively disposed at two opposite sides of the liquid storage cavity, and are respectively spatially communicated with the airflow path.

Alternatively, the electronic cigarette further includes a base seat. The base seat is accommodated and fixed in the second sleeve body. A fixing sleeve part extends from the extending portion toward the base seat. A gap is formed between the base seat and the fixing sleeve part along a lengthwise direction of the atomizing sheath. An end of the atomizing core is received in the fixing sleeve part, and the opposite other end of the atomizing core is received in the base seat. Atomizing liquid stored in the transitional storage cavity enters the atomizing passageway of the atomizing core via the gap to be atomized.

Alternatively, the communicating through hole is set as two communicating through holes. The two communicating through holes are respectively located at two opposite sides of the airflow path.

Alternatively, the electronic cigarette further includes an inhaling nozzle assembly. The inhaling nozzle assembly is disposed at one end of the atomizing sheath to seal the liquid storage cavity. An aerosol outlet is disposed on the inhaling nozzle assembly to be spatially communicated with the at least one aerosol output passageway.

Alternatively, the inhaling nozzle assembly includes a nozzle. The nozzle includes a main body and a connecting piece extending from the main body toward the extending portion. A first protrusion is disposed at a distal end of the connecting piece. A second protrusion is disposed at the atomizing sheath to be engaged with the first protrusion, and the nozzle and the atomizing sheath are therefore undetachably engaged with and fixed to each other.

Alternatively, the inhaling nozzle assembly further includes a sealing piece. A sealing sleeve part extends from the main body toward the extending portion. The sealing sleeve part is received in the liquid storage cavity. The sealing piece surrounds and is disposed outside the sealing sleeve part.

Alternatively, a communication hole is disposed on the sealing piece. A vent is disposed at a sleeve wall of the sealing sleeve part. The communication hole and the vent are spatially communicated with each other.

Alternatively, the outer housing is hollow. A circumferential wall of the outer housing includes at least one window. The atomizing sheath is made by transparent material. A remaining quantity of atomizing liquid stored in the atomizing sheath is viewable from the at least one window.

In comparison with the above existing technology, the extension portion is disposed in the atomizing sheath in accordance with the present invention. The extending portion has a hollow structure therein and forms the airflow path penetrating the wall of the atomizing sheath. The airflow path is used to spatially communicate the atomizing passageway in the atomizing core with the at least one aerosol output passageway outside the atomizing sheath. As a result, a technical solution to discharge aerosol produced in an atomization sleeve into an air outlet channel outside the atomization sleeve is achieved. A design to dispose the at least one aerosol output passageway outside the atomizing sheath is achieved. A volume of the liquid storage cavity in the atomizing sheath is increased and a liquid storage quantity of the electronic cigarette is therefore increased.

BRIEF DESCRIPTION OF THE DRAWINGS

One or more embodiments in accordance with the present invention are illustratively exemplified for explanation through figures shown in the corresponding attached drawings. These exemplified descriptions do not constitute any limitation on the embodiments. The elements with the same reference numerals in the attached drawings are denoted as similar elements. Unless otherwise stated, the figures in the attached drawings do not constitute any scale limitation.

FIG. 1 shows a schematic cross-sectional perspective view of an electronic cigarette in accordance with a preferred embodiment of the present invention.

FIG. 2 shows a schematic cross-sectional perspective view of an outer housing of an electronic cigarette in accordance with a preferred embodiment of the present invention.

FIG. 3 shows a schematic cross-sectional perspective view of an atomizing sheath of an electronic cigarette viewed from a preset viewing angle in accordance with a preferred embodiment of the present invention.

FIG. 4 shows a schematic cross-sectional perspective view of the atomizing sheath of the electronic cigarette of FIG. 3 viewed from another preset viewing angle in accordance with a preferred embodiment of the present invention.

FIG. 5 shows a schematic exploded perspective view of an inhaling nozzle assembly of an electronic cigarette in accordance with another preferred embodiment of the present invention.

FIG. 6 shows a schematic cross-sectional perspective view of an inhaling nozzle assembly of an electronic cigarette in accordance with a preferred embodiment of the present invention.

Illustration of reference numerals in attached drawings in accordance with a preferred embodiment of the present invention is as follows.

| | | | |
|---|---|---|---|
| Electronic Cigarette 100 | Outer Housing 1 | Window 10 | Atomizing Sheath 2 |
| Liquid Storage Cavity 20 | First Sleeve Body 21 | Separating Wall 211 | Aerosol Output Passageway 212 |
| Second Protrusion 213 | Extending Portion 22 | Communicating Through Hole 220 | Fixing Sleeve Part 221 |
| Opening 222 | Airflow Path 223 | Second Sleeve Body 23 | Transitional Storage Cavity 230 |
| Base Seat 3 | Air Intake Passageway 30 | Gap 31 | Atomizing Core 4 |
| Atomizing Passageway 40 | Porous Body 41 | Heating Body 42 | Support Seat 5 |
| Seat Body 51 | Peripheral Wall 52 | Inhaling Nozzle Assembly 6 | Nozzle 61 |
| Aerosol Outlet 610 | Main Body 611 | Connecting Pillar 612 | Sealing Sleeve Part 613 |
| Vent 6130 | Engaging Wall 614 | Connecting Piece 615 | First Protrusion 616 |
| Sealing Piece 62 | Bottom Wall 621 | Communication Hole 6210 | Sleeve Wall 622 |
| Battery Assembly 7 | Controlling Assembly 8 | Lampshade 9 | |

DETAILED DESCRIPTION OF PREFERRED EMBODIMENT

In order to facilitate best understanding of the present invention, the present invention will be illustrated in more detail below in conjunction with the attached drawings and preferred embodiments. It should be noted that when an element is expressed as "being fixed to" another element, this element may be directly on the another element, or there may be one or more intervening elements between this element and the another element. When an element is expressed as "being connected to" another element, this element can be directly connected to the another element, or there may be one or more intervening elements between this element and the another element. In addition, terminology used in the specification, such as "up", "down", "left", "right", "inside", "outside", or similar expressions, is only used for descriptive purposes.

Unless otherwise defined, any technical and scientific terminology used in this specification has the same meaning as commonly understood by those skilled in the technical field of the present invention. Terminology used in this specification of the present invention is only for a purpose of describing specific embodiments, and is not used to limit the present invention. Terminology such as "and/or" used in this specification includes any and all combinations of one or more related listed items.

Atomizing liquid disclosed in the present invention can be liquid tobacco, medicine ingredients in a liquid state, or other aromatic ingredient substances volatile due to heating.

Referring to FIG. 1, an electronic cigarette 100 in accordance with a preferred embodiment of the present invention mainly includes an outer housing 1, an atomizing sheath 2, a base seat 3, an atomizing core 4, a support seat 5, an inhaling nozzle assembly 6, a battery assembly 7, a controlling assembly 8 and a lampshade 9.

Referring to FIGS. 1-2, the outer housing 1 is a lengthwise hollow cylindrical structure, i.e., a length of the outer housing 1 is much larger than a diameter of the outer housing 1. A circumferential wall of the outer housing 1 has at least one window 10. In the preferred embodiment, the outer housing 1 has six windows 10 in total. The six windows 10 are divided into two sets. Each of the two sets has three windows 10 therein. A center connecting line of the three windows 10 is parallel to a lengthwise direction of the outer housing 1, i.e., the three windows 10 are equidistantly disposed on the outer housing 1 along the lengthwise direction of the outer housing 1. Each window of one of the two sets is located at a same height location as a corresponding window of the other of the two sets.

Figure 2:
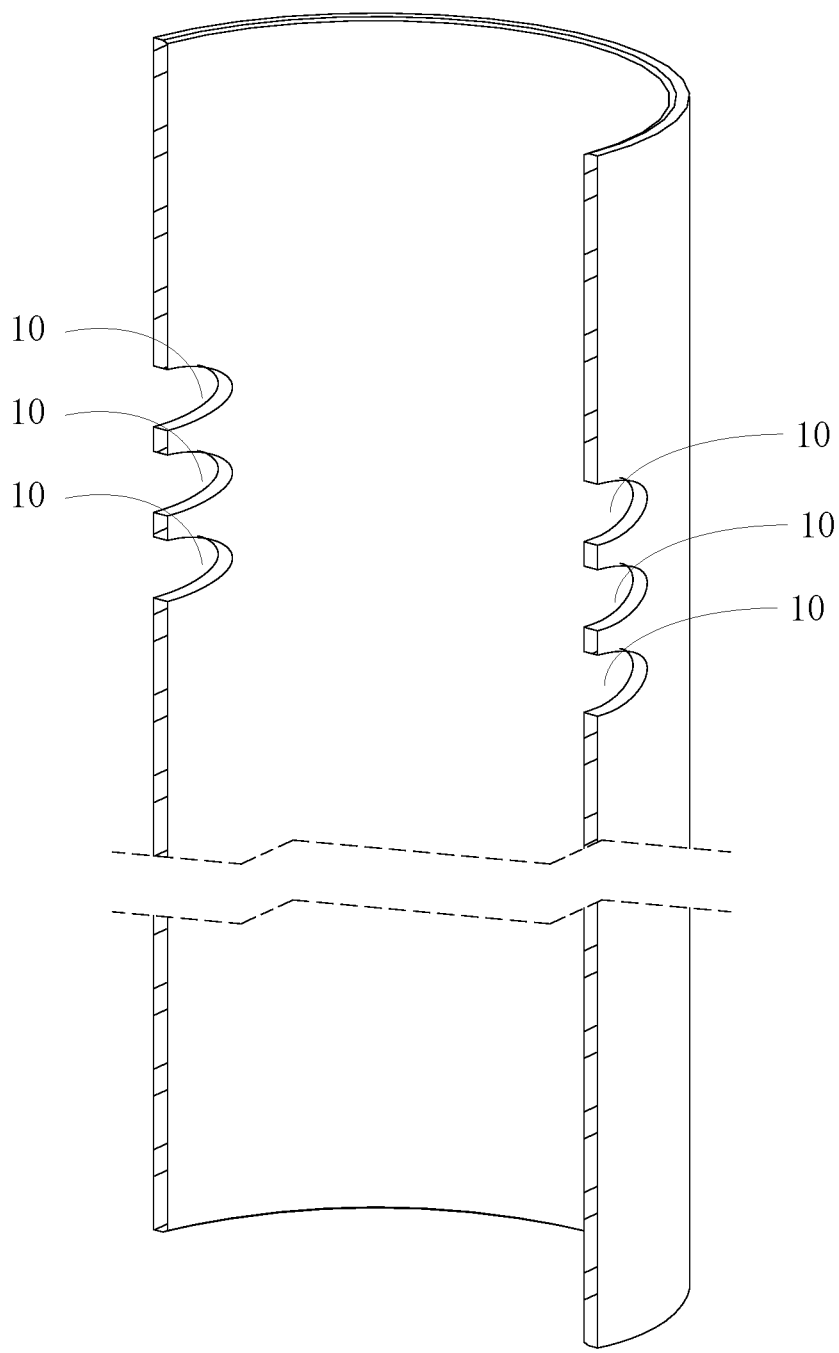
Figure 3:
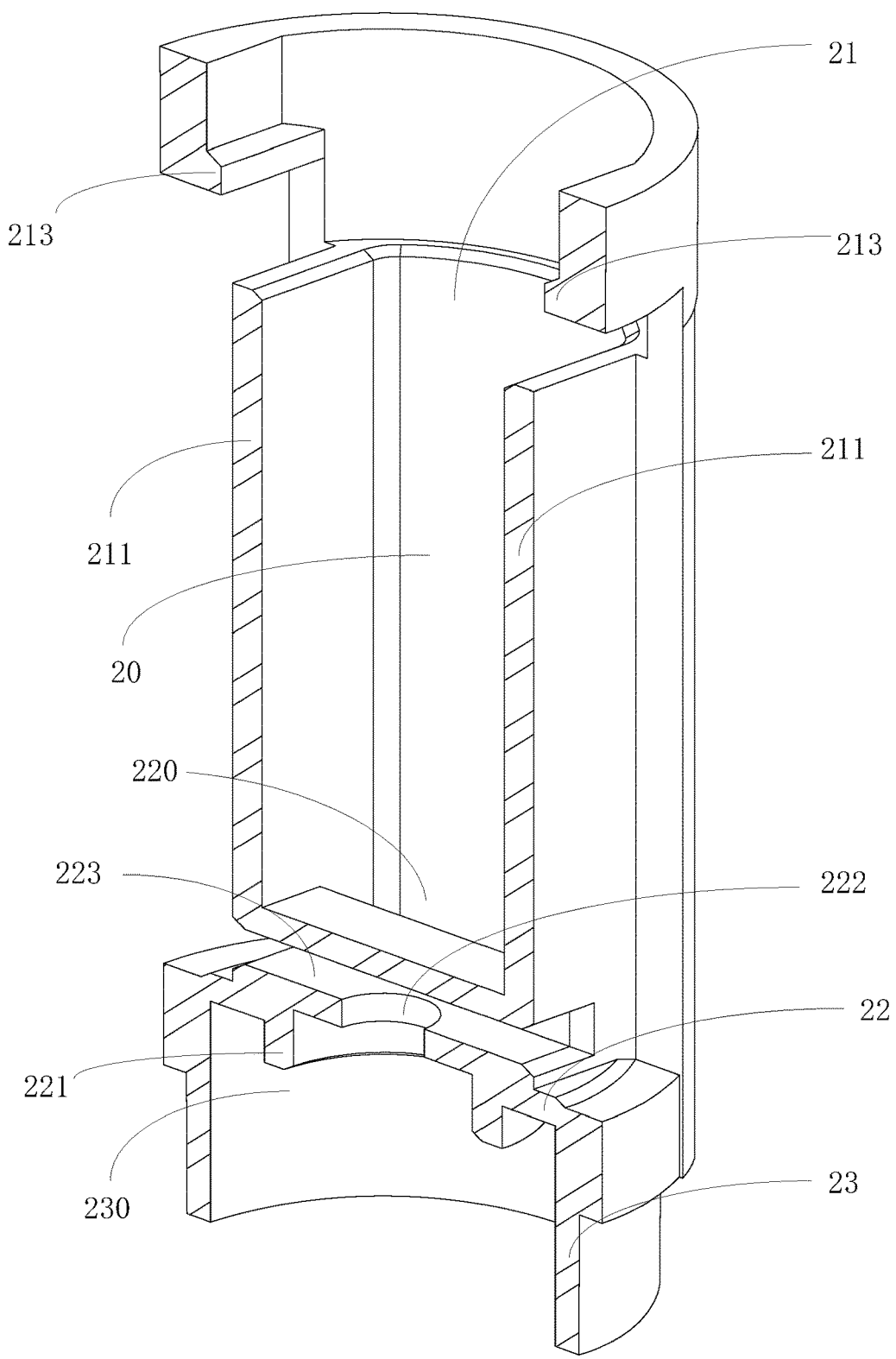
Figure 4:
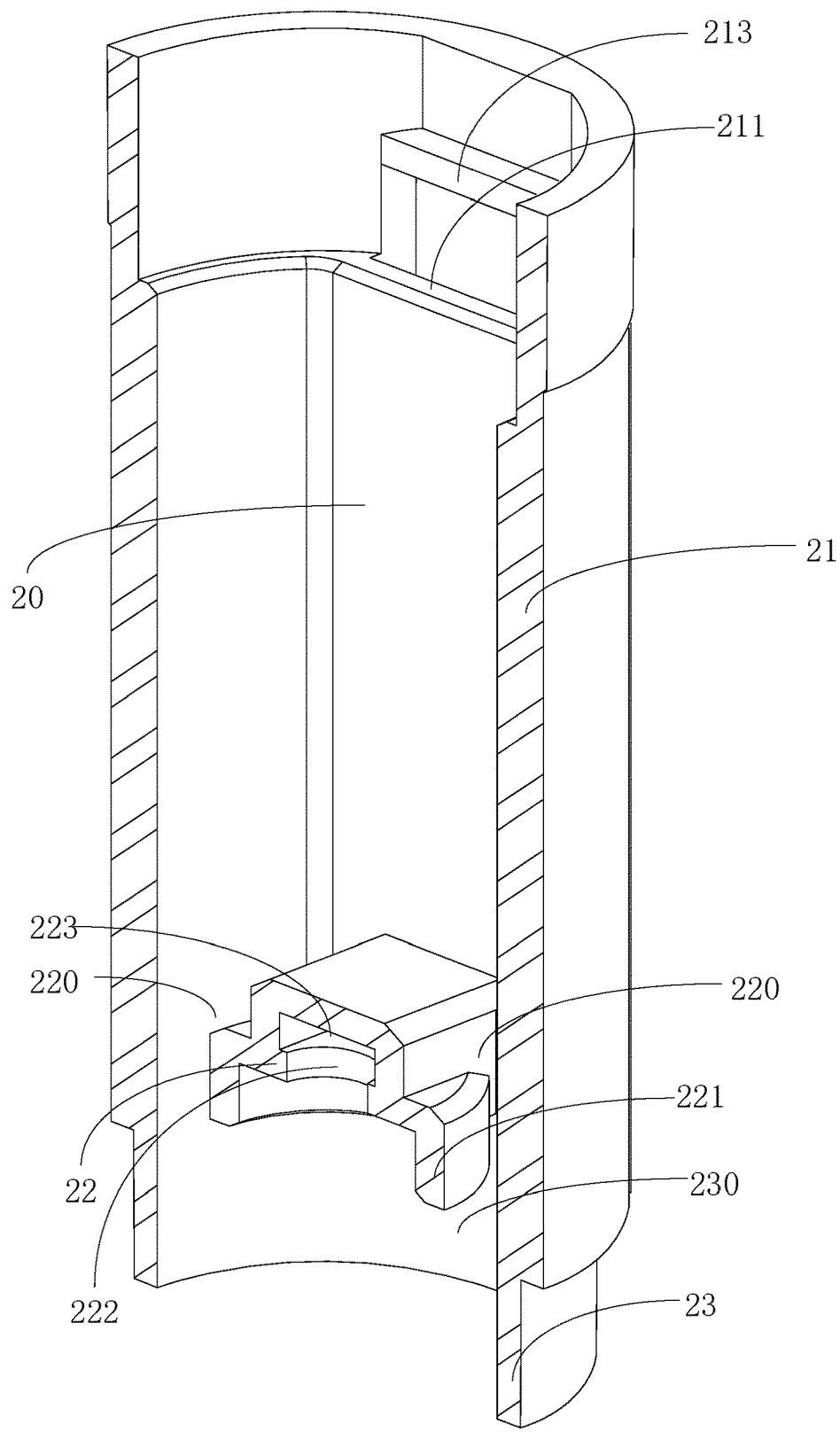

Referring to FIGS. 1 and 3-4, the atomizing sheath 2 is received and fixed in the outer housing 1. A length of the atomizing sheath 2 is smaller than the length of the outer housing 1. An upper edge of the atomizing sheath 2 is substantially flush with an upper edge of the outer housing 1. An outer wall of the atomizing sheath 2 is attachably fixed to an inner wall of the outer housing 1.

The atomizing sheath 2 is made by transparent and high-temperature tolerant plastic material, such as material of poly(1,4-cyclohexylene dimethylene terephthalate glycol) (Shorted for "PCTG"). PCTG is an amorphous copolyester. A commonly used comonomer in PCTG is cyclohexane dimethanol (CHDM), and therefore a full name of PCTG is poly(1,4-cyclohexylene dimethylene terephthalate glycol). PCTG is a polycondensation product under transesterification using three monomers including terephthalic acid (PTA), ethylene glycol (EG) and cyclohexane dimethanol (CHDM). In comparison to polyethylene terephthalate (PET), PCTG additionally includes a comonomer of cyclohexane dimethanol. In comparison to poly(1,4-cyclohexamethylene dimethylene terephthalate) (PCT), PCTG additionally includes a comonomer of ethylene glycol.

The atomizing sheath 2 is substantially lengthwise cylindrical. An extending portion 22 extends inwards from an inner wall of the atomizing sheath 2 to divide the atomizing sheath 2 into a first sleeve body 21 and a second sleeve body 23. The extending portion 22 does not completely block the first sleeve body 21 from the second sleeve body 23 so that the first sleeve body 21 and the second sleeve body 23 are spatially communicated with each other.

Two separating walls 211 are disposed in the first sleeve body 21. The two separating walls 211 are parallel to each other and oppositely disposed. The two separating walls 211 and the first sleeve body 21 cooperatively surround a space therebetween to form a liquid storage cavity 20. Aerosol output passageways 212 are disposed outside the separating walls 211, i.e., two aerosol output passageways 212 are respectively disposed at two opposite sides of the liquid storage cavity 20. Either one of the two aerosol output passageways 212 is cooperatively surrounded to be formed by the first sleeve body 21, a corresponding one of the two separating walls 211 and the outer housing 1. An upper edge of either one of the two separating walls 211 is lower than an upper edge of the first sleeve body 21. An indentation is formed and located above the either one of the two separating walls 211. A second protrusion 213 is disposed to extend toward a center of the first sleeve body 21 from an inner wall of an upper edge of the indentation.

The extending portion 22 is located below the first sleeve body 21, and extends along a radial direction of the first sleeve body 21. Communicating through holes 220 are respectively formed between front and rear sides of the extending portion 22 and an inner wall of the first sleeve body 21, i.e., two communicating through holes 220 are disposed at the extending portion 22. A fixing sleeve part 221 extends from the extending portion 22 along a direction facing away from the first sleeve body 21, i.e., the fixing sleeve part 221 extends downwards from the extending portion 22. An opening 222 are disposed at a location of the extending portion 22 corresponding to the fixing sleeve part 221. An airflow path 223 is disposed above the fixing sleeve part 221 and extends along a radial direction of the atomizing sheath 2. The airflow path 223 is spatially communicated with the two aerosol output passageways 212 located at its left and right sides. The airflow path 223 is located between the two communicating through holes 220 at its front and rear sides, i.e., the two communicating through holes 220 are respectively located at two opposite sides of the airflow path 223.

The second sleeve body 23 is formed to extend from the extending portion 22 along the direction facing away from the first sleeve body 21, i.e., the second sleeve body 23 extends downwards from the extending portion 22. A length of the second sleeve body 23 is smaller than a length of the first sleeve body 21. The fixing sleeve part 221 is accommodated in the second sleeve body 23. A transitional storage cavity 230 is formed in the second sleeve body 23. The two communicating through holes 220 of the extending portion 22 are respectively spatially communicated between the liquid storage cavity 20 and the transitional storage cavity 230. Since the transitional storage cavity 230 is located below the liquid storage cavity 20, atomizing liquid stored in the liquid storage cavity 20 will flow to enter the transitional storage cavity 230 through the two communicating through holes 220 due to gravity. As a result, the atomizing liquid is transiently stored in the transitional storage cavity 230.

The base seat 3 is accommodated and fixed in the second sleeve body 23. The base seat 3 is made by material of silica gel. An outer wall of the base seat 3 is snugly engaged for being fixed on an inner wall of the second sleeve body 23 in order to seal the transitional storage cavity 230. The base seat 3 includes an accommodating cavity and an air intake passageway 30 penetrating between upper and lower sides of the base seat 3. A gap 31 is formed between the base seat 3 and the fixing sleeve part 221 along a lengthwise direction of the atomizing sheath 2.

The atomizing core 4 includes a porous body 41 and a heating body 42. The porous body 41 is used to absorb atomizing liquid stored in the liquid storage cavity 20 and transiently store the absorbed atomizing liquid therein, i.e., function of the porous body 41 is conducting atomizing liquid. After being electrified, the heating body 42 heats atomizing liquid stored in the porous body 41 to generate aerosol for direct inhaling of users. The porous body 41 is a hollow cylindrical structure. In the preferred embodiment, the porous body 41 is made by porous ceramic. Understandably, the porous body 41 can be also made by foamed metal, porous glass or hard glass fiber tube. The heating body 42 is integrally formed in an inner cavity of the porous body 41. The heating body 42 is made by electrically connective metal material. Material to make the heating body 42 can be nickel, ferro nickel alloy, ferro chrome aluminum alloy, nickel chrome alloy, stainless steel or titanium alloy, etc.

An upper end of the porous body 41 is received and fixed in the fixing sleeve part 221. A lower end of the porous body 41 is received and fixed in the base seat 3. Atomizing liquid stored in the transitional storage cavity 230 flows to the porous body 41 through the gap 31 between the fixing sleeve part 221 and the base seat 3, and is permeantly conducted from an outer side of the porous body 41 to an inner side of the porous body 41 in order to be further heated and atomized by the heating body 42. As a result, aerosol is formed in an atomizing passageway 40 of the atomizing core 4 for direct inhaling of users.

The support seat 5 is used to support the base seat 3. The support seat 5 includes a seat body 51 and a peripheral wall 52 extending upwards from the seat body 51. An upper end face of the seat body 51 is engaged with a lower end face of the base seat 3. An air intake hole is disposed at a center of the seat body 51 to penetrate through the seat body 51 between an upper side of the seat body 51 and a lower side of the seat body 51. The air intake hole is spatially communicated with the air intake passageway 30. The peripheral wall 52 surrounds around an outside of the second sleeve body 23. The support seat 5 is made of plastic material having a certain strength, such as being made of material of ethylene-vinyl acetate copolymer (EVA).

Figure 5:
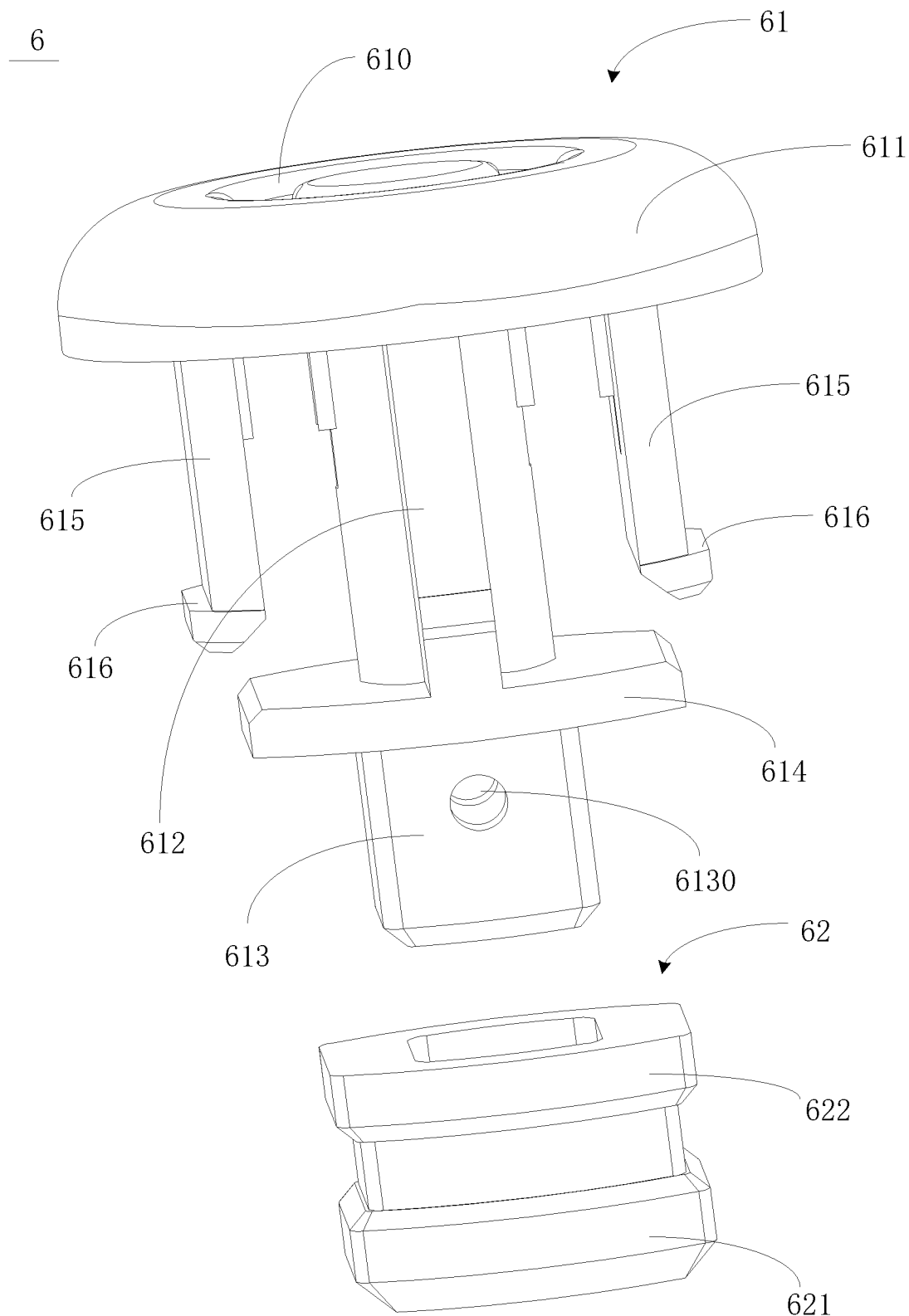
Figure 6:
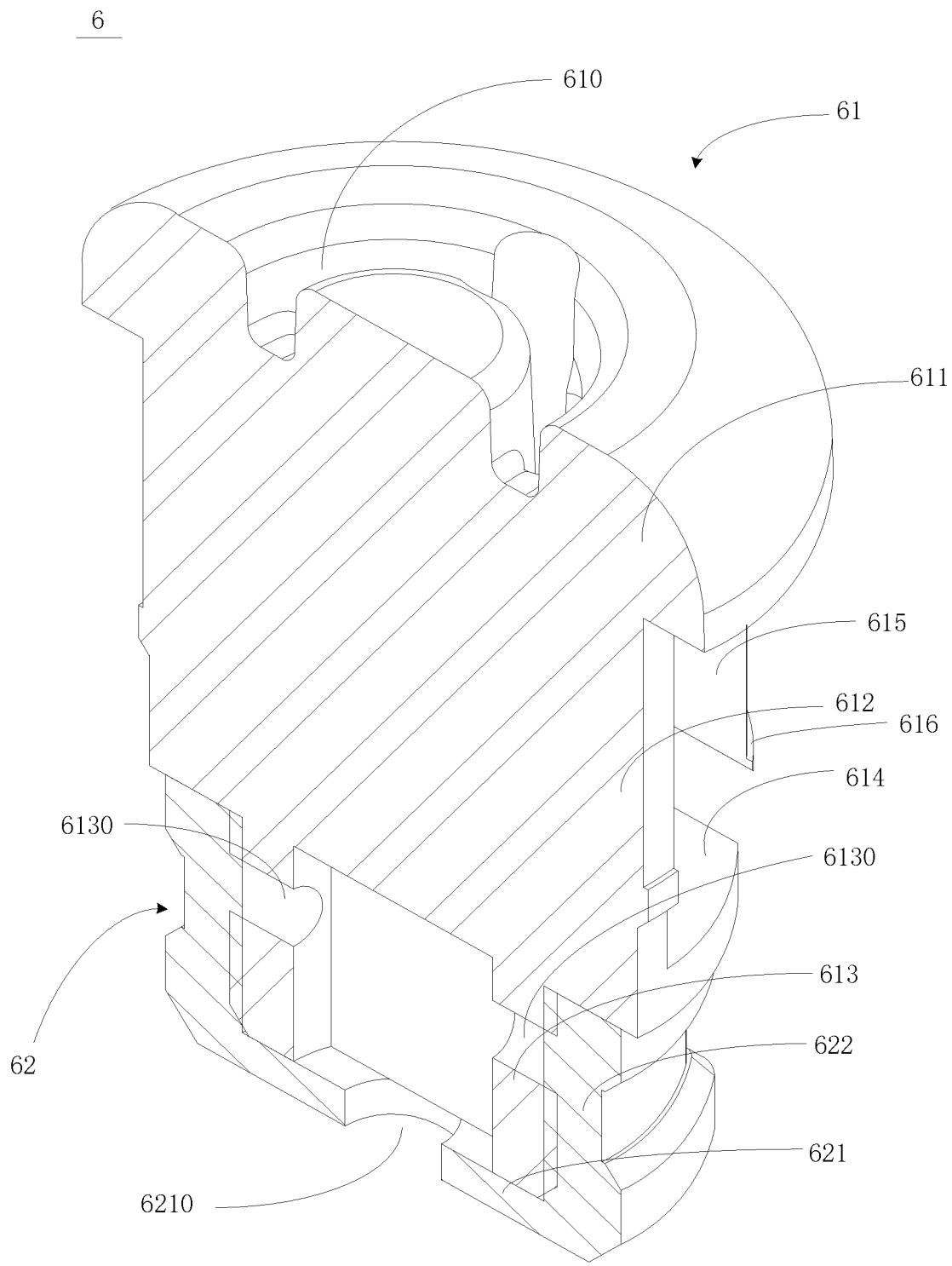

Referring to FIGS. 1 and 5-6, the inhaling nozzle assembly 6 includes a nozzle 61 and a sealing piece 62. The nozzle 61 includes a main body 611. A lower end face of the main body 611 is engaged with an upper end face of the outer housing 1. A connecting pillar 612 extends downwards from a center of the main body 611. A sealing sleeve part 613 extends below the connecting pillar 612. Two vents 6130 are disposed on the sealing sleeve part 613. The two vents 6130 are respectively located at two opposite sides of the sealing sleeve part 613. An engaging wall 614 is disposed outside a connecting location of the sealing sleeve part 613 and the connecting pillar 612. The engaging wall 614 is engaged with an upper end face of the fixing sleeve part 221.

Two connecting pieces 615 extend downwards from the main body 611. The two connecting pieces 615 are respectively located at two opposite sides of the connecting pillar 612. Each of the two connecting pieces 615 has a certain resilience and toughness. A first protrusion 616 extends at a distal end of the each of the two connecting pieces 615 along a direction facing away the connecting pillar 612. The first protrusion 616 and the second protrusion 213 are engaged with each other. As a result, the nozzle 61 and the atomizing sheath 2 are undetachably connected.

An aerosol outlet 610 penetrating the main body 611 between upper and lower sides of the main body 611 is disposed in the main body 611. The aerosol outlet 610 is spatially communicated with the two aerosol output passageways 212.

The sealing piece 62 is made by material of silica gel which has excellent resilience and ductility. The sealing piece 62 can be resiliently deformed when being squeezed and/or pressed. The sealing piece 62 includes a bottom wall 621 and a sleeve wall 622 extending upward from the bottom wall 621. A communication hole 6210 is disposed on the bottom wall 621 of the sealing piece 62. The sleeve wall 622 surrounds and is disposed outside the sealing sleeve part 613. The sealing sleeve part 613 is received in the liquid storage cavity 20. The sealing piece 62 is used to seal a clearance between the sealing sleeve part 613, the two separating walls 211 and the first sleeve body 21. The communication hole 6210 is spatially communicated with the liquid storage cavity 20 and the two vents 6130.

When the inhaling nozzle assembly 6 is not yet assembled with the atomizing sheath 2, a certain clearance is formed between the sleeve wall 622 of the sealing piece 62 and the sealing sleeve part 613. During a process of the inhaling nozzle assembly 6 being gradually inserted into the atomizing sheath 2, remain air in the liquid storage cavity 20 will be discharged out of the liquid storage cavity 20 successively via the communication hole 6210 of the sealing piece 62, the two vents 6130 of the sealing sleeve part 613 and the clearance between the sleeve wall 622 of the sealing piece 62 and the sealing sleeve part 613. As a result, an upward force applied on the inhaling nozzle assembly 6 is avoided being generated by the remain excess air in the liquid storage cavity 20 being compressed, and the nozzle 61 is avoided being pushed out due to the remain air in the liquid storage cavity 20.

After the inhaling nozzle assembly 6 is completely assembled with the atomizing sheath 2, the sleeve wall 622 of the sealing piece 62 is located between the two separating walls 211 and the sealing sleeve part 613 and is squeezed and pressed to extend and deform so that the sleeve wall 622 can fill and block the clearance between the sealing sleeve part 613 and the first sleeve body 21. As a result, the atomizing liquid in the liquid storage cavity 20 can be avoided to leak from an upper side of the liquid storage cavity 20.

The battery assembly 7 is received in and fixed to the outer housing 1. A clearance is formed between an outer wall of the battery assembly 7 and the inner wall of the outer housing 1, and external air can enter the air intake hole of the support seat 5 through the clearance. The battery assembly 7 is located below the support seat 5. The battery assembly 7 is mainly used to supply electrical power to the heating body 42, and the heating body 42 generates heat after being electrified. As a result, atomizing liquid absorbed by the porous body 41 from the gap 31 between the fixing sleeve part 221 and the base seat 3 is heated.

The controlling assembly 8 is received in and fixed to the lampshade 9. The lampshade 9 is located at a lower end of the outer housing 1. The controlling assembly 8 is used to control connection or disconnection between the heating body 42 and the battery assembly 7. In a preferred embodiment of the present invention, the controlling assembly 8 can be a condenser microphone. Since a working principle of the condenser microphone is a common knowledge in the technical area, i.e., electrification of the heating body 42 to heat being controlled by the condenser microphone based on a sucking and inhaling action of users at the nozzle 61 is an existing technology in the technical area, details regarding the working principle of the condenser microphone is no longer repeated herein.

A clearance is formed between the lampshade 9 and the outer housing 1. When users suck or inhale at the nozzle 61, the condenser microphone controls the heating body 42 being electrified to heat, and external air enters the atomizing passageway 40 successively through the clearance formed between the outer housing 1 and the lampshade 9, the clearance formed between the outer housing 1 and the battery assembly 7, the air intake hole of the support seat 5 and the air intake passageway 30 of the base seat 3. The entering air in the atomizing passageway 40 can further carry aerosol generated in the atomizing passageway 40 to enter the airflow path 223 through the opening 222 of the extending portion 22. Subsequently, the air carrying the aerosol is divided by the airflow path 223 to respectively flow into the two aerosol output passageways 212 located at left and right two sides of the atomizing sheath 2. Finally, the air carrying the aerosol enters a mouth cavity or nasal cavity of users through the aerosol outlet 610 to provide the users with senses of stimulation and satisfaction.

In the present invention, the extension portion 22 is disposed in the atomizing sheath 2 in accordance with the present invention. The extending portion 22 has a hollow structure therein and forms the airflow path 223 penetrating a wall of the atomizing sheath 2. The airflow path 223 is used to spatially communicate the atomizing passageway 40 in the atomizing core 4 with the at least one aerosol output passageway 212 outside the atomizing sheath 2. As a result, a technical solution to discharge aerosol generated in the atomizing sheath 2 to the at least one aerosol output passageway 212 outside the atomizing sheath 2 and a design to dispose the at least one aerosol output passageway 212 outside the atomizing sheath 2 can be achieved. A volume of the liquid storage cavity 20 in the atomizing sheath 2 is increased and a liquid storage quantity of the electronic cigarette 100 is therefore increased. In the present invention, an end of the atomizing core 4 is fixed to the base seat 3, and the other end of the atomizing core 4 is fixed to the fixing sleeve part 221. Atomizing liquid in the liquid storage cavity 20 enters the atomizing passageway 40 of the atomizing core 4 through the gap 31 between the fixing sleeve part 221 and the base seat 3 to be atomized and form aerosol for directly inhaling and sucking. As a result, no outer sleeve tube is required to be disposed outside the atomizing core 4 of the electronic cigarette 100 in accordance with the present invention. Production cost of the electronic cigarette 100 is reduced and competition power in the market of the electronic cigarette 100 is enhanced.

It should be noted that the specification of the present invention and its accompanying drawings provides preferred embodiments of the present invention. However, the present invention can be implemented in many different forms and is not limited to the preferred embodiments described in this specification. Examples, the preferred embodiments are not intended to make additional restrictions on the content of the present invention, and the purpose of providing the preferred embodiments is to make understanding of the disclosure of the present invention become more thorough and comprehensive. In addition, the above technical features continue to be combined with one another to form various embodiments not listed above, the combinations are all regarded as being within the scope of the description of the present invention. Furthermore, for those of ordinary skill in the art, improvements or transformations can be made based on the above descriptions, and all these improvements and transformations should belong to the protection scope of the appended claims of the present invention.

What is claimed is:

1. An electronic cigarette, comprising:
    an outer housing;
    an atomizing sheath received in the outer housing, at least one aerosol output passageway being defined between the outer housing and the atomizing sheath;
    an extending portion extending inwards from an inner wall of the atomizing sheath to divide the atomizing sheath into a first sleeve body and a second sleeve body for respectively storing atomizing liquid therein, the extending portion blocking incompletely the first sleeve body from the second sleeve body so that the first sleeve body and the second sleeve body are spatially communicated with each other;
    an atomizing core disposed in the second sleeve body, an atomizing passageway being formed in the atomizing core, the atomizing core used to atomize the atomizing liquid for generating aerosol and releasing the generated aerosol into the atomizing passageway;
    wherein the extending portion is a hollow structure to form an airflow path penetrating a wall of the atomizing sheath, the airflow path is used to spatially communicate the atomizing passageway with the at least one aerosol output passageway.

2. The electronic cigarette as claimed in claim 1, wherein the extending portion extends perpendicularly to a lengthwise direction of the atomizing sheath, a liquid storage cavity is formed in the first sleeve body, a transitional storage cavity is formed in the second sleeve body, a communicating through hole is disposed on the extending portion to spatially communicate the liquid storage cavity with the transitional storage cavity.

3. The electronic cigarette as claimed in claim 2, wherein the first sleeve body comprises two separating walls, the at least one aerosol output passageway is separated to become two aerosol output passageways respectively formed between the two separating walls and the outer housing, the two aerosol output passageways are respectively disposed at two opposite sides of the liquid storage cavity, and are respectively spatially communicated with the airflow path.

4. The electronic cigarette as claimed in claim 3, wherein the electronic cigarette further comprises an inhaling nozzle assembly, the inhaling nozzle assembly is disposed at one end of the atomizing sheath to seal the liquid storage cavity, an aerosol outlet is disposed on the inhaling nozzle assembly to be spatially communicated with the at least one aerosol output passageway.

5. The electronic cigarette as claimed in claim 4, wherein the inhaling nozzle assembly comprises a nozzle, the nozzle comprises a main body and a connecting piece extending from the main body toward the extending portion, a first protrusion is disposed at a distal end of the connecting piece, a second protrusion is disposed at the atomizing sheath to be engaged with the first protrusion, and the nozzle and the atomizing sheath are undetachably engaged with and fixed to each other.

6. The electronic cigarette as claimed in claim 5, wherein the inhaling nozzle assembly further comprises a sealing piece, a sealing sleeve part extends from the main body toward the extending portion, the sealing sleeve part is received in the liquid storage cavity, the sealing piece surrounds and is disposed outside the sealing sleeve part.

7. The electronic cigarette as claimed in claim 6, wherein a communication hole is disposed on the sealing piece, a vent is disposed at a sleeve wall of the sealing sleeve part, the communication hole and the vent are spatially communicated with each other.

8. The electronic cigarette as claimed in claim 2, wherein the electronic cigarette further comprises a base seat, the base seat is accommodated and fixed in the second sleeve body, a fixing sleeve part extends from the extending portion toward the base seat, a gap is formed between the base seat and the fixing sleeve part along a lengthwise direction of the atomizing sheath, an end of the atomizing core is received in the fixing sleeve part, and the opposite other end of the atomizing core is received in the base seat, atomizing liquid stored in the transitional storage cavity enters the atomizing passageway of the atomizing core via the gap to be atomized.

9. The electronic cigarette as claimed in claim 2, wherein the communicating through hole is set as two communicating through holes, the two communicating through holes are respectively located at two opposite sides of the airflow path.

10. The electronic cigarette as claimed in claim 1, wherein the outer housing is hollow, a circumferential wall of the outer housing comprises at least one window, the atomizing sheath is made by transparent material, a remaining quantity of atomizing liquid stored in the atomizing sheath is viewable from the at least one window.

* * * * *